United States Patent [19]

Levy

[11] Patent Number: 5,102,234
[45] Date of Patent: Apr. 7, 1992

[54] MULTI-POCKET BAG FOR MEDICAL SPECIMEN

[76] Inventor: Abner Levy, 325 N. Oakhurst Dr., P4, Beverly Hills, Calif. 90210

[21] Appl. No.: 675,540

[22] Filed: Mar. 25, 1991

[51] Int. Cl.⁵ .............................................. B65D 30/22
[52] U.S. Cl. .................................... 383/38; 383/40; 383/84; 383/209
[58] Field of Search ................ 383/38, 39, 40, 85, 383/35, 38, 84, 86; 206/610; 229/72

[56] References Cited

U.S. PATENT DOCUMENTS

| 1,211,025 | 1/1917 | Wright | 383/38 |
|---|---|---|---|
| 2,175,508 | 10/1939 | Mandelbaum | 229/72 |
| 2,354,820 | 8/1944 | McCarty | 229/72 |
| 3,045,088 | 6/1963 | Blaikie et al. | 206/610 |
| 3,381,888 | 5/1968 | Schleutermann et al. | 229/72 |
| 3,685,645 | 8/1972 | Kawaguchi | 383/38 |
| 3,891,138 | 6/1975 | Glas | 383/38 |
| 3,939,971 | 2/1976 | Tulis | 383/38 |
| 4,149,667 | 4/1979 | Riley | 229/72 |
| 4,190,161 | 2/1980 | Gendron | 229/72 |
| 4,679,688 | 7/1987 | Söderhold et al. | 383/38 |
| 4,744,673 | 5/1988 | Nakamura | 383/38 |
| 4,762,230 | 8/1988 | Croce | 229/DIG. 5 |
| 4,765,485 | 8/1988 | Perkins | 229/84 |
| 4,785,940 | 11/1988 | Wilson | 206/610 |
| 4,836,382 | 6/1989 | Schreiber | 229/72 |
| 4,927,405 | 5/1990 | Martin et al. | 383/38 |
| 4,967,952 | 11/1990 | Roessiger | 229/87.19 |
| 4,993,844 | 2/1991 | Robinson et al. | 383/63 |
| 5,007,744 | 4/1991 | Scarberry et al. | 383/37 |
| 5,014,852 | 5/1991 | Herrington | 206/554 |

Primary Examiner—Stephen P. Garbe
Assistant Examiner—Christopher J. McDonald
Attorney, Agent, or Firm—Beehler & Pavitt

[57] ABSTRACT

A medical specimen bag is made of three or more overlying sheets of clear pliable plastic material joined along three common edges to make at least two separate pockets open along a fourth edge of the sheets. One of the sheets includes an adhesive flap foldable against the exposed fourth edges of the remaining sheets for sealing all the pockets. The sealed end of the bag is torn off to regain access to all pockets.

7 Claims, 1 Drawing Sheet

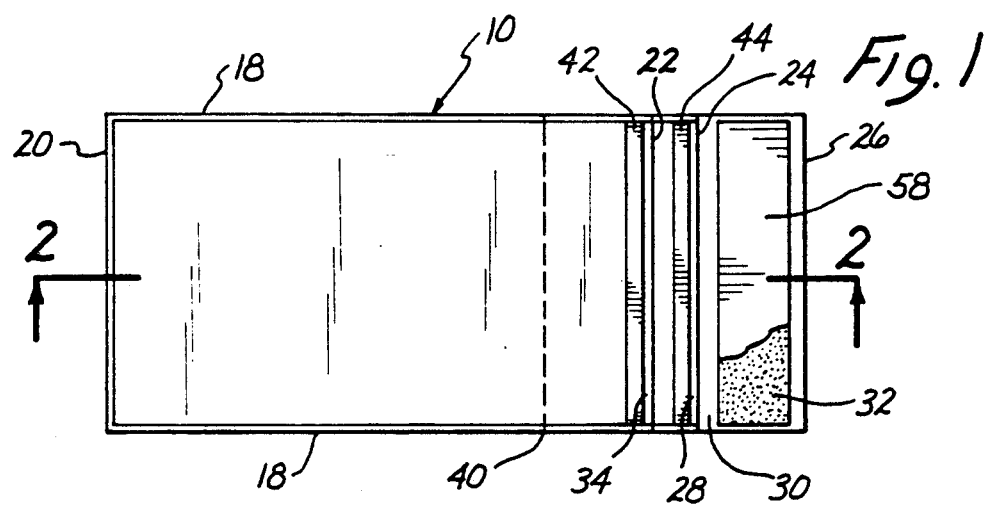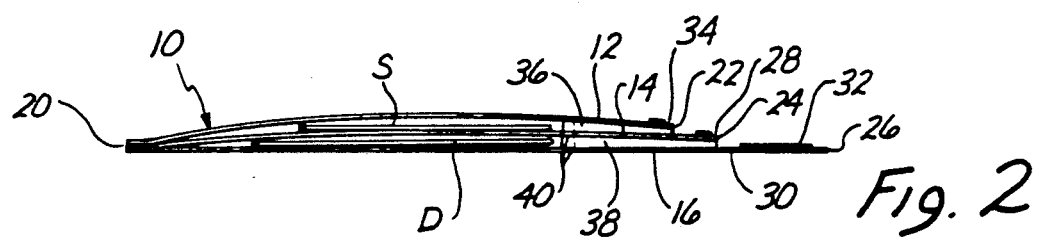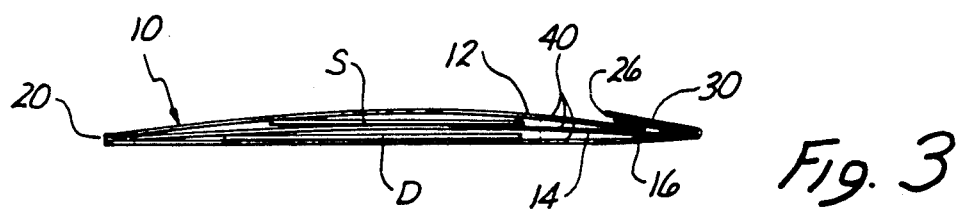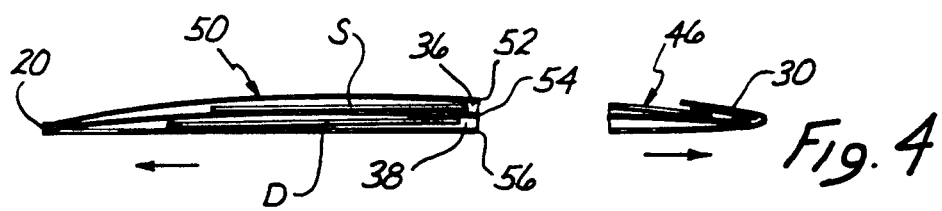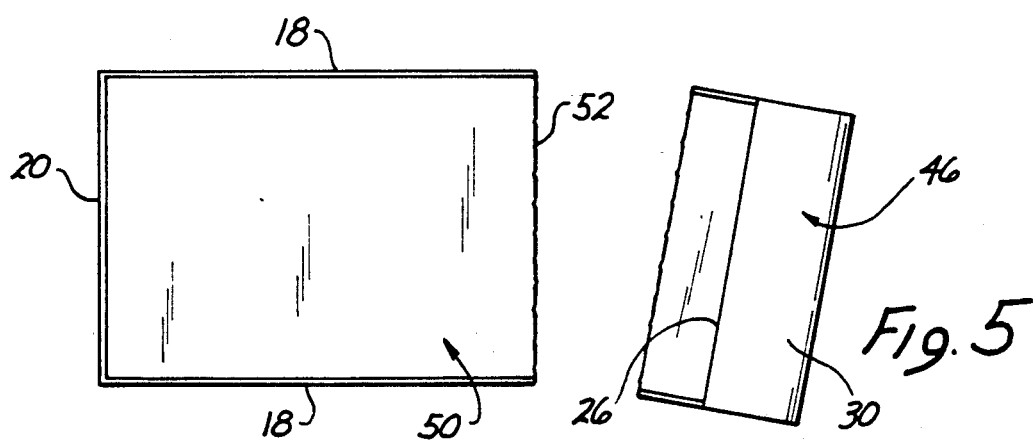

MULTI-POCKET BAG FOR MEDICAL SPECIMEN

FIELD OF THE INVENTION

This invention pertains to the field of disposable packages for biological and medical specimens and more particularly relates to a disposable bag for conveying medical specimens from a specimen collecting site to a laboratory for analysis.

BACKGROUND OF THE INVENTION

It is widespread practice in the medical field to collect specimens such as blood samples or specimens of other fluids and tissues from patients at one location, such as a doctor,s office and then conveying the collected specimens to another site, such as medical laboratory, removed from the specimen collecting site, for analysis and diagnostic study. Such specimen typically include a glass vial containing the blood sample or other fluid and is commonly accompanied by documentation which identifies the patient from whom the sample was taken and specifying the analysis or study to be performed on the specimen.

Currently, the specimen is often placed together with documentation, such as a laboratory request form, in a plastic bag which keeps the documentation together with the specimen for correlation to the corresponding patient, and also to an extent protects both the documentation and the specimen against lost and damage.

A significant shortcoming of current practice is the possibility that the vial containing the fluid sample may leak in the bag, staining the laboratory request form or documentation bearing the patient name and identification. If the patient,s identification is rendered unreadable as a result, a considerable delay may occur until the physician realizes that no laboratory report has arrived for the particular sample. By then, it is necessary to obtain a new specimen, which requires the patient to again visit the specimen collection site and undergo unpleasant collection procedure. The result is unnecessary delay, inconvenience and added expense to the patient. In a worst case scenario, the delay, in an apparently routine medical examination, may be substantial enough so that a diagnosis is made at a point in time where more difficult of medical treatment becomes necessary for the patient, and where prognosis for recovery might be less favorable. In addition, stained documentation accompanying the specimen may be a source of possible contagion to personnel who handle the documentation, if the specimen contains contagious organisms.

A continuing need exists for a dependable, easy to use and economical disposable bag for conveying medical specimens between two sites which will avoid the aforementioned difficulties and shortcomings of bags used for this purpose at this time.

SUMMARY OF THE INVENTION

These and other shortcomings of the prior art are by the present invention, which provides a multipocket bag for conveying medical specimens from a specimen collecting site to a specimen analysis site, which bag comprises at least three overlying sheets of impermeable plastic or equivalent synthetic material, joined to make at least two separate pockets open at one or both ends of the bag. One or more flaps are provided for sealing the pockets after the medical specimen and the accompanying documentation have been placed into corresponding pockets of the bag. Each sheet of the bag has a tear line, which is in register with the tear lines of the other sheets. The contents of the bag are retrieved by tearing open the bag along the tear line into two pieces, which tearing opens all the pockets at the same time.

The medical specimen, which typically is a glass vial of whole blood sealed by a rubber stopper, may be placed in one pocket. The accompanying paperwork, with the name of the patient and the responsible physician, are placed in the other pocket of the bag.

In a preferred form of the invention, one of the sheets defines a flap foldable over the free edge of the remaining sheets for closing the pockets. An adhesive or other fastening, retentive material or device is provided for retaining the flap to each of the remaining sheets along the free edge. A tear line is defined by a sequence of sheetweakening indentations or small perforations in each sheet, to facilitate manual detachment and separation of one end of the bag including a portion of each sheet, from the remainder of the bag in order to reopen and regain access into all of the pockets upon such detachment.

It is contemplated that the pockets may open at a common end of the bag and be sealable by a single flap, or, in alternate forms of the invention, may open at opposite ends of the bag and be sealable by corresponding flaps at each end. Also, two or more stacks of overlying pockets may be joined side to side. For example, a four pocket bag can be constructed with two sets of stacked pockets joined along a center seal line. Such a bag would be constructed from three sheets of plastic joined along three edges, open along a fourth free edge, and further joined along a center line between the free edge and an edge opposite to the free edge.

In a preferred construction of the novel bag, the length of the sheets increases successively from the front sheet to the bottom sheet, for exposing a margin along the free edge of each sheet, with the rear sheet being of sufficient length to define a flap foldable over all exposed margins of the other sheets, including a margin along the free edge of the top sheet. Preferably, the inside surface of the flap has a layer of pressure sensitive adhesive which is wide enough to make contact with exposed margins of each sheet, along the free edge of these sheets, so as to simultaneously seal all of the pockets in the bag when the flap is folded over and pressed down against the exposed margins. The pressure sensitive adhesive on the flap will normally be covered and protected by a release sheet which is pulled off by the user to expose the adhesive, just prior to closing and sealing of the bag.

In the closed condition of the flap, the adhesive seal between the flap and each three edge of the remaining sheets effectively closes and partitions the interior of the bag into sealed pockets fully isolated from each other, and secure against fluid leakage from one pocket to another.

A tear line extends across the width of each sheet, preferably parallel to the free edge of each sheet. Together, the tear lines facilitate easy and quick detachment of an end of the bag, including a portion of each sheet, to regain access into all of the pockets upon such detachment. The seal between the flap and each free edge of the remaining sheets serves to transmit the pulling, tearing force to the tear line in each of the sheets, including the intermediate sheets of the bag.

In typical use, the medical technician will place the biological or medical specimen in one of the pockets, e.g. the front pocket and the documentation, laboratory request. etc. in the other, then fold the flap into sealing engagement with the exposed margins of each remaining sheet, to seal both pockets from each other as well as the exterior environment. The specimen may then be conveyed in the bag to a laboratory or the like, where personnel simply tears the bag along the tear line for easy and immediate access to all pockets. Even with the reclosed flap end torn away, a useful bag structure remains which safely holds the specimen and accompanying documentation for easy removal.

It is preferred to use a clear plastic material such as clear polyethylene sheeting for making the bag of this invention, to allow easy viewing of the bag contents while it is sealed. In order to facilitate use of the bag, a colored stripe or equivalent indicia may be printed or otherwise applied to a margin area along the free edge of each sheet, to highlight and make the free edge readily visible to the user, for easier separation of the sheets at their free edges and for quick identification of each pocket in the bag when inserting material.

These and other advantages of the present invention will be better understood by reference to the following description of the preferred embodiments and the accompanying drawings.

BRIEF DESCRIPTION OF THE DRAWINGS

FIG. 1 is a front plan view of a two-pocket medical specimen bag according to the present invention;

FIG. 2 is a longitudinal section taken along line 2—2 in FIG. 1;

FIG. 3 is a longitudinal section as in FIG. 2 but showing the flap folded in closed condition, sealing both pockets of the bag;

FIG. 4 is a section as in FIGS. 2 and 3, but showing the flap end of the bag torn away and detached from the rest of the bag to reopen both pockets for access to their contents;

FIG. 5 is a plan view as in FIG. 2, but showing the flap in closed, sealing condition, and the flap end of the bag torn away as in FIG. 4.

DETAILED DESCRIPTION OF THE PREFERRED EMBODIMENT

With reference to the attached drawings, FIG. 1 shows a two-pocket bag 10 according to the present invention. The bag 10 is comprised of three overlying sheets, best seen in FIG. 2, including a front sheet 12, an intermediate sheet 14 and a rear sheet 16. The three sheets are joined, as by a heat seal, along three common edges, including side edges 18 and end edge 20. Each sheet has a fourth, free edge 22, 24, and 26 respectively. The three overlying sheets define two pockets, a front pocket 36 between front sheet 12 and intermediate sheet 14. and a rear pocket 38 between the intermediate sheet 14 and rear sheet 16. In an initial condition of the bag, the pockets are sealed and joined along edges 18, 20 of the sheets. The two pockets are both open for access into their interiors at the free edges 22, 24 of the respective sheets. FIGS. 2 through 4 show, by way of example, a medical specimen S in the front pocket 36 and accompanying documentation D in the rear pocket 38.

The length of each sheet, 12, 14, 16 successively increases, starting with the front sheet 12 towards the rear sheet 16, as measured from the closed end 20 to the flap edge 26. The successive increase in sheet length exposes a marginal area 28 of the intermediate sheet 24, and also defines a flap 30 at the free end 26 of the rear sheet 16. Flap 30 can be folded over the free edges 24, 22 of the remaining sheets 14, 12 respectively to make an adhesive bond between the adhesive layer 32 on the flap and non overlapping marginal areas 28, 34 along each free edge 24, 22 respectively of the remaining sheets. The adhesive layer 32 is initially covered and protected by a release sheet 58, shown broken away in FIG. 1 to expose the adhesive layer 32. The release sheet 58 is removed by the user to expose the adhesive layer just prior to closing of the bag to seal the contents. Sealing engagement between the flap 30 and the free edge of each sheet simultaneously closes and seals both pockets, the front pocket 36 and the rear pocket 38. The adhesive seal of the flap 30 with the margins 34, 28 complete the sealing of the pockets 36, 38 from each other as well as the outer environment, a condition illustrated in FIG. 3. In this sealed condition each pocket 36, 38 is an impermeable compartment, ensuring that even in case of leakage or spilling of fluids in one pocket, legibility of the patient identifying documents in the other will not be impaired.

In order to facilitate use of the bag, colored stripes 42, 44 are printed on sheets 12, 14 respectively adjacent to the corresponding free edges 22, 24. These colored stripes serve to highlight the location of the free edges in clear sheet material, where the edge position may be otherwise difficult to identify. The two stripes aid the user in locating the openings to each of the two pockets 36, 38 and to positively identify each pocket when placing materials into the bag.

Tear lines 40 are defined between the side edges 18 of each sheet 12, 14, and 16 parallel to the free edges of the sheet, as shown in FIGS. 1 and 2. Each tear line 40 is in register with each other when viewed in the top plan view of FIG. 1. The tear lines may be defined by weakening of the sheet material, in a manner which is known to those possessed of ordinary skill in the manufacture of plastic bags.

The seal bag of FIG. 3 is opened by tearing away a portion of each sheet, including the flap seal, as shown in FIG. 4, along the tear lines 40. The torn away end portion 46 is discarded, leaving a remaining bag portion 50 open at newly created free edges 52, 54 and 56 of sheets 12, 14 and 16 respectively. The pockets 36 and 38 are simultaneously opened by this tearing of the bag 10 for immediate access to both their interiors.

It is desirable that the adhesive defining the adhesive layer 32 make a permanent seal with the sheet material of sheets 12, 14 which cannot be broken without visibly rupturing the sheet material of the bag to prevent tampering with the contents of the bag once the flap 30 has been closed and sealed. After sealing, it is highly desirable that subsequent access to the contents of the bag be possible only by tearing open of the bag so as to assure that the medical specimen received at the laboratory is exactly as placed in the bag at the specimen collection site.

In an alternate form of this invention, flaps such as flap 30 may be provided at each end of the bag 10, so that the two pockets open at opposite ends of the bag, but both pockets can be accessed by tearing along a single tear line 40 comprised, as has been described, by individual tear lines in register on each sheet comprising the bag. More complex bags according to this invention may include more than two pockets, all opening at a common end of the bag as in the drawings, or at alternate, opposite ends of the bags so that one or more pockets are sealed by one flap at one end, and another or other pockets are sealed by a second flap at an opposite end of the bag. The flaps at opposite ends of the bag may be defined by the same sheet or by different ones of the sheets comprising the bag.

A bag structure such as shown in FIGS. 1 through 5 can be converted into a four pocket bag by providing a sheet seal line centered between the side edges 18 and extending from the initially closed end 20 to the free edge 24 of the intermediate sheet 14. In a bag having more than one intermediate sheet, this centered seal line extends to the free edge of the rearmost intermediate sheet, i.e the intermediate sheet immediately adjacent to the rear sheet 16, which carries the flap 30. The benefits described for the two-pocket embodiment of FIGS. 1 through 5 are equally available in modified forms of the invention where pockets are defined in side by side relationship.

While a preferred form of the invention has been shown and described for purposes of example and clarity, it will be understood that many changes, substitutions and modifications to the described embodiment will become apparent to those possessed of ordinary skill in the art without thereby departing from the spirit and scope of the present invention, which is defined by the attached claims.

What is claimed is:

1. A bag for conveying medical specimens from a specimen collecting site to a specimen analysis site comprising:

three or more overlying sheets of clear pliable plastic material joined along three common edges to make at least two separate pockets open along a free edge of said sheets and separated by one or more intermediate ones of said sheets, one of said sheets defining a single foldable flap engageable with the free edge of each of the remaining of said sheets for closing all of said pockets at said free edge.

2. The bag of claim 1 wherein said flap has pressure sensitive adhesive means for effecting said engaging and release sheet means normally covering said adhesive prior to said closing.

3. The bag of claim 1 further comprising perforations defining a tear line in each of said sheets for facilitating joint detachment of a portion of each of said sheets to regain access into all of said pockets upon detachment of said portion.

4. The bag of claim 1 wherein said sheets are of varying length to define non overlapping exposed margins at each said free edge, said margins being simultaneously engageable by said single flap for closing all of said pockets.

5. The bag of claim 1 furthe comprising indicia near each said free edge for easier location of the opneing to each of said pockets on clear sheet material.

6. A bag for conveying medical specimens from a specimen collecting site to a specimen analysis site comprising:

three or more overlying sheets of clear pliable plastic material joined along three common edges to make at least two separate pockets open along a fourth edge of said sheets and separated by one or more intermediate ones of said sheets, one of said sheets defining a single flap foldable over said fourth edges of the remaining of said sheets for closing said pockets;

said remining of said sheets being of successively greater length to expose non overlapping margins at each said free edge;

pressure sensitive adhesive means for permanently retaining said single flap to all of said margins;

visual indicia along said free edge of at least one of said sheets for visually highlighting the location of said fourth edge thereby to facilitate separation of said sheets at said fourth edge for access into said pockets prior to said closing; and tear line means for facilitating joint detachment of a portion of each of said sheets to regain access into all of said pockets upon detachment of said portion.

7. The bag of claim 6 further comprising release sheet means normally covering said adhesive means prior to said closing.

* * * * *